United States Patent [19]

Feller et al.

[11] 4,409,200

[45] Oct. 11, 1983

[54] REVERSE TRANSCRIPTASE FROM HUMAN MILK, METHOD FOR ITS PURIFICATION, AND ITS USE IN THE DETECTION OF BREAST CANCER

[75] Inventors: William F. Feller, Bethesda; Judith A. Kantor; Jack G. Chirikjian, both of Rockville, all of Md.; Terence M. Phillips, Washington, D.C.

[73] Assignee: Research Corporation, New York, N.Y.

[21] Appl. No.: 144,326

[22] Filed: Apr. 28, 1980

[51] Int. Cl.³ .................... G01N 33/56; G01N 33/58
[52] U.S. Cl. .......................... 436/516; 435/7; 435/15; 436/530; 436/531; 436/542
[58] Field of Search ............... 424/1, 112; 23/230 B; 435/7, 15

[56] References Cited

U.S. PATENT DOCUMENTS

| | | | |
|---|---|---|---|
| 3,899,298 | 8/1975 | Szczesniak | 23/230 B X |
| 4,072,574 | 2/1978 | Loeb et al. | |
| 4,146,603 | 3/1979 | Davidson et al. | |
| 4,160,019 | 7/1979 | Bjorklund | |
| 4,180,556 | 12/1979 | Kim et al. | |
| 4,193,981 | 3/1980 | Bjorklund | |
| 4,203,724 | 5/1980 | Sawai et al. | 23/230 B |

FOREIGN PATENT DOCUMENTS 2729893  11/1978  Fed. Rep. of Germany .

OTHER PUBLICATIONS

Gerard et al., Nature, vol. 256, Jul. 10, 1975, pp. 140–143.
Judith A. Kantor et al., "DNA Polymerase with Characteristics of Reverse Transcriptase Purified from Human Milk", Science 5/4/79, v. 204, pp. 511–513.
T. Ohno et al., "Purification and Characterization of the DNA Polymerase of Human Breast Cancer Particles", Proc. Natl. Acad. Sci. U.S.A. 74 (1977), 764–768.

*Primary Examiner*—Christine M. Nucker
*Attorney, Agent, or Firm*—Oblon, Fisher, Spivak, McClelland & Maier

[57] ABSTRACT

A method for diagnosing mammalian breast cancer by detecting in the physiological fluid of said mammal an antigen (ACRT) having immune cross-reactivity with human reverse transcriptase, or detecting antibodies against said ACRT or detecting antibody-ACRT complexes, wherein the reverse transcriptase is substantially purified, has a molecular of about 70,000 and a sedimentation coefficient on a glycerol gradient of between 5 and 5.5 S. A process for the purification of reverse transcriptase from human milk.

24 Claims, 5 Drawing Figures

REVERSE TRANSCRIPTASE FROM HUMAN MILK, METHOD FOR ITS PURIFICATION, AND ITS USE IN THE DETECTION OF BREAST CANCER

Part of the work leading to this invention was funded by a grant from the Department of Health, Education and Welfare of the United States. The United States government is granted a nonexclusive, royalty-free license.

BACKGROUND OF THE INVENTION

1. Field of the Invention

The present invention relates to a reverse transcriptase enzyme from human milk, and its use in the detection of breast cancer.

2. Description of the Prior Art

The diagnosis of human cancer has been carried out in the prior art by detecting the presence of a variety of polypeptides in human sera.

Thus, for example, Björklund, U.S. Pat. No. 4,160,019 describes the isolation of a cancer associated polypeptide antigen (CAPA) showing monospecificity and being present in a wide variety of human cancers of different localizations. The material possessing CAPA activity is isolated by homogenizing malignant tissues from autopsies, carcinoma tissues of various types and sites being collected to make a tumor pool. The purified CAPA is a polypeptide based on the single peptide chain, soluble at a pH within the range of about 1-3.5, and denaturing irreversibly at pH's exceeding about 4.5. The antigen is hygroscopic, turns yellow and becomes inactivated and smeary when it takes up moisture. The authors established that CAPA originates from cancer cell walls. The polypeptide has a molecular weight within the range of 20,000-27,000 and does not contain any carbohydrate or nucleic acid. The presence of CAPA has been detected in cancers as varied as those originated in the intestines, colon, rectum, pancreas, breast, ovaries, prostate, testes, and the like.

Freedman et al, U.S. Pat. No. 3,663,684 describe a carcinoembryonic antigen showing so-called "CEA-activity". CEA is used for detection of cancer of the colon and is extracted from the antigen-containing tissues by a glycoprotein solvent. Its molecular weight is about 200,000, although it may be as low as 70,000. It is a glycoprotein.

Davidson et al, U.S. Pat. No. 4,146,603 also describe a class of glycoproteins found to be produced by human cancer cells and present in the sera of cancer patients. This glycoprotein is called "TSGP" (tumor specific glycoprotein). TSGP is generated by tumor cells regardless of the tumor concerned. It appears in the circulatory system of humans suffering from lung, mammary, colon, uterine, or gastric carcinomas, melanomas, and the like. It is used for the early diagnosis of individuals with any kind of malignant disease.

None of the aforementioned diagnostic tests is specific for breast cancer.

The presence of a reverse transcriptase enzyme in human breast cancer tissue has been established by Gerard, G. F. et al, Nature, 256: 140-143 (1975). In 1977, Ohno et al, Proceedings of the National Academy of Sciences, USA, 74: 764-768 (1977), described the properties of a reverse transcriptase purified from human breast cancer particles. This enzyme is a DNA polymerase with reverse transcriptase properties, sedimenting between 5 and 6 S and having a molecular weight estimated about 70,000. The enzyme was purified by fractionating breast tumor for particulate material of density 1.16-1.18 g/cm$^3$, solubilizing this sample and applying it to a column of polyacrylamide agarose gel. Fractions containing the reverse transcriptase were then pooled and loaded onto a phosphocellulose column. The reverse transcriptase was then isolated by a fractionation on this column. Non-malignant samples yield no enzyme activity with the properties of the reverse transcriptase of Ohno et al. The reverse transcriptase from the Ohno et al preparation has been characterized immunologically and has been determined to be related to the reverse transcriptase of the Mason Pfizer monkey virus (Ohno et al, Proceedings of the National Academy of Sciences, USA, 74: 2144 (1977)).

Other studies (Schlom et al, Science, 175: 542 (1972), Dion, A. S. et al, Cancer Research 34: 3509 (1974), Feldman et al, Proceedings of the National Academy of Sciences, USA, 70: 1976 (1973)) have shown that some human milk samples contain RNA-dependent DNA nucleotidyl transferase activity (reverse transcriptase). The activity from human milk has, however, never been isolated, purified or immunologically characterized.

A need continues to exist for a rapid and efficient, as well as highly specific diagnostic test for the detection of human breast cancer. Such a test could be used for example, to qualify a generalized diagnosis of cancer (obtainable with the previously described tests) to a diagnosis of breast cancer.

SUMMARY OF THE INVENTION

It is therefore an object of the invention to provide a selective diagnostic test for the determination of mammalian breast cancer.

Another object of the invention is to provide a reverse transcriptase enzyme substantially purified from human milk.

Still another object of the invention is to provide a method for the purification of a reverse transcriptase enzyme from human milk.

A further object of the invention is to provide a method for detecting human breast cancer by using substantially purified reverse transcriptase enzyme from human milk in a detectably labeled form.

Still a further object of the invention is to provide detectably labeled reverse transcriptase enzyme substantially purified from human milk, antibodies raised against this enzyme, in their substantially purified form and/or in a detectably labeled form.

These and other objects of the invention which will hereinafter become more readily apparent have been attained by providing:

A method for diagnosing breast cancer in mammals by detecting, in a physiological fluid of said mammal an antigen (ACRT) having immunocross-reactivity with a human reverse transcriptase enzyme, such as that deriveable from human milk wherein said enzyme has a molecular weight of 70,000 and a sedimentation coefficient on a glycerol gradient, of 5-5.5 S.

Another object has been attained by providing a method as described above, wherein either ACRT-immune antibodies are detected or antibody-ACRT complexes are detected.

Another object has been attained by providing a reverse transcriptase enzyme substantially purified from human milk, having a MW of 70,000 and a sedimentation coefficient on glycerol gradient of 5-5.5 S.

Another object has been attained by providing a reverse transcriptase as described above, in detectably labeled form.

Another object has been attained by providing a method of purifying a reverse transcriptase from human milk containing particles of density 1.15–1.25 and which particles comprise a lipid-rich outer layer coating a core containing said reverse transcriptase in admixture with nucleic acid and other enzymes, which comprises:

- separating said particles from the main body of said human milk;
- removing said lipid-rich outer alyer by treating said particles with a phospholipase enzyme;
- separating said nucleic acid from said reverse transcriptase enzyme and said other enzymes from said core;
- purifying said reverse transcriptase from said remaining admixture of enzymes of said core.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

The present invention has succeeded in providing a highly sensitive, fast and selective method for the detection of mammalian breast cancer. The present inventors have discovered that a macromolecular antigen having cross-reactivity with human milk reverse transcriptase is present in the physiological fluids, especially the serum, of a mammal (e.g., a human) with breast cancer. The antigen will be called hereinafter ACRT (Antigen having Cross-Reactivity with Reverse Transcriptase).

The essence of the invention relates to the isolation, purification and characterization of a reverse transcriptase enzyme from the milk of normal lactating humans. This enzyme is capable of being used in a binding assay for the detection of breast cancer. The enzyme resembles reverse transcriptase of RNA tumor viruses in its primer template specificities and cation requirement (Gallagher, R. E., et al, Proceedings of the National Academy of Sciences, USA, 71: 1309 (1974), and Steel, L. K., et al, Cancer Letters, 2: 291 (1977)). The purified enzyme is devoid of terminal transferase activity and is not immunologically related to human DNA polymerases $\alpha,\beta$ or $\gamma$.

In order to prepare the enzyme, high-density particles ($\rho = 1.15–1.25$, preferably $\rho > 1.2$) are obtained from defatted human milk (Feldman, S. P., et al, Proceedings of the National Academy of Sciences, USA, 70: 1976 (1973)). Samples of human milk are pooled, defatted and centrifuged. The skim milk is filtered through cheesecloth, mixed with glycerol and centrifuged at 45,000–50,000 rev/min for 1–2 hours. After centrifugation, the sediment is separated and constitutes the milk concentrate. Particles with a density greater than about 1.2 g/cm$^3$ are prepared from the milk concentrate according to the method of Feldman, S. P. et al (Proceedings of the National Academy of Sciences, USA, 70: 1976 (1973)).

The particles contain a lipid rich membrane coat surrounding a central "core" containing nucleic acid plus the reverse transcriptase plus other enzymes. The preparation of the enzyme thus comprises removal of the lipid rich membrane followed by breaking up of the core, separation of nucleic acid therefrom and final purification of the enzyme.

In order to remove the membrane, dithiothreitol (DDT) or any other sulfhydryl-containing reducing agent is added together with a phospholipase enzyme (for example, phospholipase C, available commercially) to the milk concentrate. The solution is incubated for a few minutes, preferably 2 minutes, at about 37° C. and then for about 15–30 minutes, preferably 20 minutes, at about room temperature, preferably 25° C. The resulting solution is cooled to 0°–10° C., and a water immiscible organic solvent, such as for example, anhydrous ether, is added thereto to form an emulsion by gentle mixing. After centrifugation of the resulting emulsion, the lower aqueous phase is removed and the aqueous solution is then layered over a discontinuous metrazamide gradient (Sanner, Cancer Research, 36: 405 (1976)). Metrazamide is available commercially; the gradient consists of 1.5 volume parts of 25% metrazamide ($\rho > 1.18$), 1.0 volume parts of 18% metrazamide ($\rho > 1.10$) in a buffer containing an alkali metal halide salt such as sodium chloride, and a metal chelating agent, such as EDTA. This buffer is at a pH between 7.5 and 9.0, preferably at a pH of 8.0. An appropriate buffer is 10 mM tris-HCl (pH 8.0), 150 mM NaCl, and 2 mM EDTA. The solution which has been layered over the discontinuous metrazamide gradient is centrifuged for about 90 minutes at 45,000–50,000 rev/min at 4°–10° C. The high-density particles are resuspended in 10 mM buffer at pH 8.0, containing a detergent (1–5%) capable of breaking up the core. Non-ionic detergents, well-known to those skilled in the art are preferably used. For example, 1% N-P$_{40}$, 0.5 M KCl and particles, are gently stirred for about 1 hour at about 40° C. The sample is then desalted by standard desalting techniques such as for example, use of coarse Sephadex G-25 ®.

The reverse transcriptase activity is purified from these high-density particles by a sequential chromatography on two types of materials. The first chromatographic step rids the enzyme from contaminant nucleic acid. Any material having adsorption properties for nucleic acids can be used; for example, diethylaminoethyl-cellulose (DEAE-52 cellulose ®). Thus, desalted material containing broken up high-density milk particles is applied to DEAE-cellulose equilibrated with a buffer capable of maintaining a pH between 7.5 and 8.5. An appropriate buffer is for example, 10 mM tris-HCl (pH 7.5), 20% glycerol, 0.2% detergent and 2 mM sulfhydryl reducing agent, such as DTT. After application of the sample, the chromatographic column is washed with the buffer and the reverse transcriptase activity is batch-eluted with the buffer to which at least 0.3 M KCl have been added. Fractions having polymerase activity with $(dG)_{12-18} \cdot (C)_n$ (a hybrid of polycytidylate and deoxyguanylate that is 12 to 18 nucleotides long) as described below, are collected.

The fractions having polymerase activity are pooled, desalted and applied to the second chromatographic material, a poly(C) agarose column equilibrated in the same or different buffer.

Other chromatographic materials capable of separating reverse transcriptase from other enzymes will work. Thus, agarose coupled to synthetic polyguanylate, or synthetic polythymidilate, or synthetic polyadenylate can be used. These materials work in a "pseudo-affinity chromatography" fashion. Still other columns could be loaded with immobilized antireverse transcriptase antibody, and the like.

When using poly(C) agarose, the column is washed with buffer and the DNA polymerase activity is eluted with a linear gradient of 0 to 0.8 M KCl in the same buffer. The peak of enzyme activity elutes at about 0.20 M KCl. The fractions containing the main peak of DNA polymerase activity are pooled and ovalbumin is added to about 200 μg/ml to stabilize the enzyme. Other stabilizing materials can be bovine serum albumin, gelatin, etc. The enzyme is stable, can be kept at 40° C., and can be used for characterization studies.

The molecular weight of the DNA polymerase was determined by three methods: (i) SDS (sodium dodecyl sulfate)-polyacrylamide gel electrophoresis, (ii) Sephadex G-200 ® chromatography, and (iii) velocity sedimentation analysis. Molecular weights can be determined by using standard protein markers such as phosphorylase A (94,000), bovine serum albumin (68,000), and ovalbumin (43,000). The peak coming off the last column material, with a 200-fold purification over the high-density particles, contains a major polypeptide band corresponding to a molecular weight of about 70,000. Molecular sieving of the material through Sephadex G-200 ®, in the presence of 0.5 M KCl indicates that the human milk reverse transcriptase has a molecular weight of 70,000. The enzyme is sedimented through a linear glycerol gradient (10-30% by volume) and the enzyme active fractions are located by assaying with the primer template $(dG)_{12-18} \cdot (C)_n$. The enzyme activity sediments between 5 S and 5.5 S, slightly faster than the bovine serum albumin marker.

In order to demonstrate that the DNA polymerase isolated from human milk has reverse transcriptase activity, the following synthetic primer-template specificities were determined. In general, the viral reverse transcriptase show a preference for $(dT)_{12-18} \cdot (A)_n$ (a hybrid of polyadenylate and deoxythymidilate that is 12 to 18 nucleotides long) and not for $(dT)_{12-18} \cdot (dA)_n$ (a hybrid of poly(deoxyadenylate) and deoxythymidilate which is 12 to 18 nucleotides long (Spiegelman et al, Nature (London) 228: 430 (1970)). Reverse transcriptase will also use $(dG)_{12-18} \cdot (C)_n$ (a hybrid of poly(citydylate) and deoxyguanylate that is 12 to 18 residues long) and $(dG)_{12-18} \cdot (Cm)_n$ (a hybrid of poly(2'-O-methylcitydylate) and deoxyguanylate which is 12 to 18 residues long) as templates for the synthesis of polydeoxyguanylate (Sarngadharan, M. G., et al, Nature (London) New Biology, 240: 67 (1972); Gerard, G. F., Biochem. Biophys. Res. Commun., 63: 706 (1975)). The cellular DNA polymerases, specifically polymerase γ, will inefficiently transcribe $(dG)_{12-18} \cdot (C)_n$ at low salt concentrations, that is, 0.05 M $KH_2PO_4$ or no added KCl (Sarngadharan, M. G., et al, supra, Gerard, G. F., supra and Knopf, K. W., et al, Biochemistry 15: 4540 (1976)), and will not utilize poly(2'-O-methylcitydylate).oligodeoxyguanylate for the synthesis of poly(dG).(Knopf, K. W., et al, supra).

The response of human milk DNA polymerase to synthetic primer templates appears in Table 1. Assays are described below in the section on Examples.

TABLE 1

| Template | [³H]dNTP | Divalent cation | [³H]dNMP, polymerized (pmole) |
|---|---|---|---|
| $(A)_n \cdot (dT)_{12-18}$ | TTP | $Mn^{2+}$ | 0.16 |
| $(A)_n \cdot (dT)_{12-18}$ | TTP | $Mg^{2+}$ | 0.70 |
| $(dA)_n \cdot (dT)_{12-18}$ | TTP | $Mn^{2+}$ | 0.10 |
| $(dA)_n \cdot (dT)_{12-18}$ | TTP | $Mg^{2+}$ | 0.08 |
| $(C)_n \cdot (dG)_{12-18}$ | dGTP | $Mn^{2+}$ | 0.05 |
| $(C)_n \cdot (dG)_{12-18}$ | dGTP | $Mg^{2+}$ | 0.50 |
| $(Cm)_n \cdot (dG)_{12-18}$ | dGTP | $Mn^{2+}$ | 0.25 |
| $(Cm)_n \cdot (dG)_{12-18}$ | dGTP | $Mg^{2+}$ | 0.50 |
| Primer alone | | | |
| $(dT)_{12-18}$ | TTP | $Mg^{2+}$* | <0.01 |
| $(dT)_{12-18}$ | dGTP | $Mg^{2+}$* | <0.01 |
| $(dG)_{12-18}$ | TTP | $Mg^{2+}$* | <0.01 |
| $(dG)_{12-18}$ | dGTP | $Mg^{2+}$* | <0.01 |

*Same results with $Mn^{2+}$.
TTP: thymidine triphosphate
dGTP: deoxyguanosine triphosphate
dNTP: deoxynucleoside triphosphate
dNMP: deoxynucleoside monophosphate The response shows that the enzyme can synthesyze poly(dT) in the presence of $(dT)_{12-18} \cdot (A)_n$ and $Mg^{2+}$ (10 mM). It will also utilize templates $(dG)_{12-18} \cdot (C)_n$ and $(dG)_{12-18} \cdot (Cm)_n$ when synthesizing polydeoxyguanylate. Primer alone with either $Mg^{2+}$ or $Mn^{2+}$ gives not detectable activity. This pattern of primer template utilization by the human milk DNA polymerase excludes the possibility that it is a terminal deoxynucleotidyl transferase.

The utilization of $(dG)_{12-18} \cdot (Cm)_n$ in the presence of $Mg^{2+}$ shows that this enzyme is not a cellular polymerase found in human milk. The results show a pattern of activities that are consistent with those obtained with reverse transcriptase from animal viruses (Sarngadharan, M. G., et al, supra; Gerard, G. F., supra).

Further characterization of the DNA polymerase with reverse transcriptase activity can be carried out by immunochemical methods. An antibody is prepared against the purified DNA polymerase from human milk and the IgG fraction is obtained by standard methods. One or two micrograms of the immune IgG inhibit the DNA polymerase 70% but do not inhibit polymerase α,β or γ from human milk. A number of enzyme neutralization studies can be carried out with purified polymerases α and γ from other human sources. Neither DNA polymerase α from human lymphoid cells nor DNA polymerase γ from NC-37 cells or from HeLa cells are inhibited by the antibody to human milk DNA polymerase. An antibody binding to polymerase γ (IgG fraction) can be obtained, which binds to the enzyme to form an antigen-antibody complex but does not neutralize activity (Robert-Guroff, M. and Gallo, R. C., Biochemistry 16: 2874 (1977)). Binding is assayed with the antibody (IgG) to polymerase γ and the human milk DNA polymerase. Complex formation can be determined by velocity sedimentation through linear glycerol gradients. The fractions are assayed for DNA polymerase activity and the shape and position of the curve can be compared to control gradients. When this test is carried out, the DNA polymerase having reverse transcriptase activity from human milk does not bind to the antibody to polymerase γ. The γ polymerase from HeLa cells and NC-37 cells do not bind to the antibody to human milk DNA polymerase. This indicates that this last polymerase is not immunologically related to polymerases α, β, or γ from human sources.

When the human milk reverse transcriptase is compared immunologically to the reverse transcriptases of some RNA viruses, enzyme neutralization studies with antibody to reverse transcriptase against simium sarcoma virus, baboon endogoneous virus and RD-114, are all negative.

All of these results indicate that the reverse transcriptase isolated from high-density particles of human milk is immunologically distinct from DNA polymerases α, β, or γ. The enzyme has no terminal transferase activity, as indicated by its inability to incorporate either $^3$H-labeled deoxyguanosinemonophosphate or $^3$H-labeled thymidinemonophosphate when oligodeoxyguanylate or oligodeoxythymidilate is used as a primer.

The present inventors have discovered that patients with breast cancer exhibit in their serum an antigen (ACRT) which is immunologically cross-reactive with the reverse transcriptase from human milk described above. Furthermore, in patients with breast cancer, the antigen may be present in the serum by itself, or in the form of an antibody-antigen complex. In addition, freely circulating antibody against ACRT may also be present in cancer patients. This indicates that the detection of ACRT in mammalian serum, by itself of in complexation with antibodies, or detection of the antibodies themselves, serve as a selective diagnostic test for breast cancer. Such a diagnostic test can be carried out by standard well known binding assay methodology.

When ACRT is detected in mammalian serum, it is possible to incubate a sample of mammalian serum containing the ACRT with a dissociatable complex of a binding macromolecule and a detectably labeled reverse transcriptase purified from human milk as described above. Among the detectable labels useable in the present invention are radiolabels, enzyme labels, chromophoric labels, or other labels.

Radiolabels for example, can be divided into two types: those with an internal label and those with an external label. With an internal label, an existing atom in the reverse transcriptase enzyme is replaced by a radioactive isotope of that atom (e.g.: $C^{14}$ for $C^{12}$, $H^3$ for $H^1$). With an external label, an atom or atoms of a radioactive isotope (e.g., $I^{131}$ or $I^{125}$) are substituted for an existing atom on the reverse transcriptase; to achieve stability, a covalent link is established between the enzyme and the label. The enzyme with an external label such as $I^{125}$ is not identical with the unlabeled enzyme, but its behavior is practically indistinguishable from the latter. Both the internal or external label methodology can be used in the present invention. The most preferred method is that of using an external label, most preferably radioactive iodine. It is known that iodine can be substituted into the aromatic side-chain of tyrosine residues, as well as other amino acids such as histidine. Many procedures have been described for iodination, and they can all be used in the present invention. The most common technique is the chloramine T technique (Greenwood, F. C. et al, Biochemical Journal, 89: 114 (1963)). This procedure is simple since all that is required is mixing a solution of the substantially purified reverse transcriptase, sodium iodide having radioactive iodine and chloramine T; the reaction is terminated by the addition of a reducing agent, preferably sodium metabisulfite.

For a general description of labeling techniques, see Chard: "An Introduction to Radioimmunoassay and Related Techniques", North Holland Publishing Co., Amsterdam, N.Y., Oxford, 1st Edition, 1978.

Labels other than radioactive labels can, of course, be used since they are well known in generalized binding assay techniques. Thus, for example, alternatives to isotopic labels may be (a) chromophoric labels: such as fluorescent, ultraviolet absorbing or visible light-absorbing labels. These are advantageous because of their long shelf life and absence of radiation. (b) Enzyme labels: since specific enzymes can be coupled to other molecules by covalent links, a highly specific enzyme may be covalently reacted with the substantially purified reverse transcriptase (see for example, Engvall et al, "Enzyme-Linked Immunoabsorbent Assay.Elisa", the Journal of Immunology, vol. 109: 120 (1972)). (c) Other tracers: such as free radical labels or bacterial labels can also be used in the present invention.

In order to carry out a competitive binding assay, such as a colorimetric assay or a radioimmunoassay, it is necessary to provide a binding macromolecule which has reversible affinity for the detectably labeled-containing reverse transcriptase. Such a binding macromolecule is most generally an antibody raised against reverse transcriptase substantially purified from human milk. It is also obvious that the binding macromolecule, preferably antibody, should as far as possible be directed only to the reverse transcriptase which the assay is intended to measure, not to a wide variety of similar materials which would intefere with specificity. Human antibodies or "hybridoma" antibodies from human or animal sources could of course also be used.

The preparation of anti-sera in animals is a well known technique (Chard, supra, pp. 385-396). The choice of animal is usually determined by a balance between the facilities available, and the likely requirements in terms of volume of the resulting anti-serum. A large species such as goat, donkey and horse may be preferred because of the larger volumes of serum readily obtained; however, it is also possible to use smaller species such as rabbits or guinea pigs which often have high titer anti-sera. Usually, subcutaneous injection of substantially purified reverse transcriptase coupled to guinea pig albumin and emulsified in Freund's complete adjuvent is sufficient to produce anti-reverse transcriptase anti-sera. The detection of antibodies can be carried out by testing the anti-sera with appropriate detectably labeled reverse transcriptase. Fractions that bind labeled reverse transcriptase are isolated and further purified if necessary.

It is of course possible to use other than antibodies as the binding macromolecule. The use of cell receptors specific for reverse transcriptase or of any circulating binding proteins equally specific for reverse transcriptase can be used.

The general competitive binding assay techniques useful for the detection of minute amounts of organic molecules, such as hormones, proteins, antibodies, and the like are well known in the art (Chard, supra). Any of these competitive binding assay techniques can be used for the purposes of the present invention. A small amount of serum from a patient suspected of having breast cancer is incubated with a complex of the detectably labeled reverse transcriptase and the binding macromolecule. If ACRT is present in the sample serum, it will displace detectably labeled reverse transcriptase from the binding macromolecule binding sties and "free" the labeled enzyme. It is then necessary to determine the distribution of labeled enzyme between the free and the bound form. Usually, but not always, this requires that the bound fraction be physically separated from the free fraction; a variety of techniques can be used for that purpose. All of the techniques exploit physical-chemical differences between the labeled enzyme and its free and bound form. The general available methodologies have been described by Yalow (Pharmacol. Rev. 28: 161 (1973)). These techniques include adsorption of free antigen to solid phase material, such as cellulose, charcoal, silicates or ion exchange resins; precipitation of antigen-antibody complexes by second antibody; salting out techiques or organic solvents; adsorption or complexing of antibody to solid phase material; electrophoretic separation on cellulose, starch gel or polyacrylamide gel, and the like.

The choice of technique depends on the speed, simplicity, applicability and cost. It is a simple matter of choice for anyone skilled in the art and therefore, the generalized techniques will not be described in further detail.

Particularly preferred among the aforementioned techniques are adsorption methods, double-antibody methods and solid phase systems.

In adsorption methodology, the non-specific adsorption of proteins to particle surfaces is used as a method for the separation of bound and free detectably labeled enzyme. The procedure depends on the fact that only the labeled enzymes and not the binding macromolecules or bound complexes have the adsorption property. The most preferred adsorption procedure, which is highly useful in the present case, is adsorption on charcoal or silicates. The most commonly used of the available charcoals are the Norit range (Norit SX1) with a maximum particle size of 63 μm.

"Double" or "second" antibody methods depend on the precipitation of the bound complex with an antibody directed to the binding macromolecule. The second antibody is specific to the γ-globulin of the species in which the first antibody was raised, for example, if a guinea pig anti-reverse transcriptase is used in the primary reaction of an assay for ACRT, an antibody to guinea pig γ-globulin raised in a goat may be used for the separation step. Although most commonly used in radioimmunoassays, this concept can be applied to any binding macromolecule for which an antibody is available. Separation by this technique requires a relatively large concentration of second antibody and a correspondingly large amount of the species of γ-globulins of which the first antibody forms a part must be included; for this purpose, a second antibody system always involves the addition of carrier protein, either whole serum or γ-globulin from the species in which the first antibody was raised. The use of coupling of the second antibody to an insoluble matrix such as cellulose is more economical and efficient and has been described by den Hollander et al (Kirkham et al, "Radioimmunoassay Methods" 419 (1971)).

Solid phase systems in general have been increasingly utilized in recent years. When the binding macromolecule is covalently coupled to an insoluble support, both it and the bound complex can readily be separated from the soluble free fraction. A wide variety of solid phase supports have been described which include particles of dextran and cellulose, and continuous surfaces such as polystyrene or polypropylene discs, or the walls of plastic or glass tubes. Plastic surfaces exhibit adsorptive properties, and simply exposing such surface to an appropriate dilution of the immunoglobulin antibody, e.g., IgG, will lead to the attachment of a proportion of the antibody molecules thereon. The bond is probably ionic or hydrophobic and not covalent. Covalent bonding, however, can be readily obtained by the incorporation of crosslinking agents such as glutaraldehyde and other agents in the antibody solution used for the coating. Coated tube systems offer great convenience in the actual performance of assays and the technique can be widely used in commercial kits. In one preferred embodiment, the antibody is covalently attached to the inside of a test tube and labeled enzyme is also incorporated in the tube. A single addition of a sample of fluid being tested is then added to the test tube. After incubation, the contents of the tube are emptied and the tracer is detected by standard methodology.

The binding macromolecule can also be attached to a particulate solid phase by any one of a number of techniques designed to yield a covalent link between the protein and the particles, such as for example, diazotization or cyanogen bromide activation. The resulting material is then extensively washed to insure that no free γ-globulin molecules remain. Alternative approaches include the use of antibody entrapped in the interstices of a polyacrylamide gel or covalently bound to magnetic particles (polymer-coated iron oxide). With the latter system, mixing and separation can be simply achieved by the application of a magnetic field.

After incubation of the test sample with the binding macromolecule-labeled enzyme complex, and separation of the labeled enzyme, it is necessary to detect the label by some physical or chemical means. When the label is a second enzyme, said second enzyme is assayed by the addition of a substrate which upon reaction releases a ultraviolet or visible light-absorbing product. Thus, for example, the second enzyme may be alkaline phosphatase. To the conjugate reverse transcriptase-alkaline phosphatase is added a solution of p-nitrophenylphosphate at pH 8.0. p-Nitrophenylphosphate has substantially no absorbance at 400 nm. However, on being acted upon by alkaline phosphatase, the substrate releases p-nitrophenol which has a large absorption coefficient at 400 nm and is yellow. In such a simple fashion then, appearance of yellow coloration is a direct indication of the presence of ACRT in the serum of the patient.

When the label is radioactive iodine, scintillation counting is the method of choice. Radioactive iodine is a γ-ray emitter and therefore intimate contact between the isotope and the scintillator is unnecessary. The scintillator in these cases usually consists of a crystal of sodium iodide coated with thallium usually formed as a well; as the radiation strikes, the molecules making up the crystal lattice, ionization occurs and results in a light flash which is then detected by the photomultiplier. If the radioisotope used for labeling is $C^{14}$ or $H^3$, liquid scintillation is appropriate to detect $\beta$-particles.

Patients having breast cancer may also contain freely circulating antibody against ACRT. In such case, a sample of serum from the patient suspected of having breast cancer, is mixed with a large excess of detectably labeled reverse transcriptase. After an appropriate incubation time, sufficient to allow formation of antibody enzyme complexes, bound complexes and antibodies are separated from excess remaining labeled enzyme. This is carried out by adsorbing excess labeled enzyme onto an appropriate material having adsorbing capacity therefor but not adsorbing capacity for complex or free antibody. The non-adsorbed solution can then be assayed by the appropriate methodology (radioactivity or colorimetric, or the like) for the presence of detectably labeled antibody-reverse transcriptase complex. It is also possible to prepare an immobilized reverse transcriptase by binding the enzyme to an insoluble support. Incubation of the resulting insoluble enzyme with a sample of serum will cause antibody therein to bind to the insoluble support. In order to detect the bound antibody, a double antibody or second antibody technique is utilized. The second antibody is raised against reverse transcriptase immune IgG. The second antibody is then detectably labeled, for example, with a radioactive label or with an enzyme. Incubation of the second antibody with the insolubilized antibody enzyme complex will cause attachment of the second antibody to the insoluble support. After washing remaining soluble second antibody, the solid insoluble support is detected by radioactivity measurement or by appropriate enzyme assay. When an enzyme assay is used, this technique is the well known Elisa technique (Engvall et al, Journal of Immunology, vol. 109: 129 (1972)). A preferred embodiment of the system is achieved by coating a tube with reverse transcriptase and then adding a sample of serum thereto, followed by an enzyme-labeled preparation of anti-immune reverse transcriptase IgG. The enzyme activity remaining in the tubes after washing provides a measurable amount of specific antibodies in the serum. Coating of polystyrene tubes is a preferred embodiment. Another preferred embodiment is the attachment of reverse transcriptase to the surface of a cellulose of plastic strip. Incubation of this strip with a serum sample containing reverse transcriptase immune IgG and further incubation of the resulting strip with detectably labeled anti-reverse transcriptase immune IgG will attach the second detectably labeled antibody to the strip. Washing of the strip and counting thereof (if radiolabeled is used) or incubation of the strip with a drop of appropriate color-generating substrate (if enzyme labeled is used) will indicate the presence of antibody against ACRT in the serum of the patient.

A complex of ACRT and complementary antibody has been found to be present in breast cancer patients. Therefore, methods for the detection of the antibody enzyme complex are also part of the present invention.

A preferred method is to dissociate the antibody-antigen complex into its free components and analyze those separately by the methods discussed previously. For example, a sample of serum from a patient suspect of having breast cancer is mixed with 3 parts by volume of a solution of polyethyleneglycol (PEG) in 10% saline buffer, wherein the PEG is of molecular weight 6000. The final concentration of PEG should be 1-10%, preferably 2-5% by volume. The addition of PEG to the serum, precipitates $C_{lq}$ binding-IgG complexes which comprise fully formed complement binding complexes (true complexes) and initial complement binding complexes (precursor complexes). The precipitate of PEG and complexes is separated from the supernatant and deposited on top of a 10-50% gradient of PEG, molecular weight 20,000, in saline phosphate buffer pH 7.2, 0.01 M phosphate. The centrifuge tube is ultra-centrifuged with the aid of a $W^2T$ integrator capable of maintaining a constant value of the g rating at 10,000±2000 xg for 10-30 minutes, preferably about 20 minutes. The ultra-centrifugation causes the material to develop into a series of bands. The bands are fractionated from the tube by a standard fraction recovery system and the band between 20 and 22% contains the ACRT-containing complex. This band is isolated and the complexes are separated from the PEG. Standard separation of PEG from the complexes can be carried out for example, by film electrophoresis. The contents of the 20-22% band are acidified to a pH 2.5 with an appropriate buffer. The acidification step separates the complexes into antigen and antibody components but, the presence of PEG, prevents the loss of the tertiary structure of these components. The acidified mixture is then added to a block of agarose (normally 2-5 mm thick, 10 cm long), into a well or channel formed at the center thereof. Standard agarose useful for high endosmotic flow (for example, sigma type $3^R$) can be used. Electrophoresis for 1 hour in 0.5 M sodium barbital buffer pH 8.6 is carried out at 1 mamp/cm. The antigen moves to the anode while the antibody moves to the cathode and the PEG remains in the well or trough. All that remains is to detect the antibody or antigen at the cathode or anode respectively, by any of the previously discussed methods. Thus, for example, the anode fraction of the agarose is cut and suspended in a beaker with saline, and further detection of the ACRT can be carried out. Alternatively, a cellulose acetate membrane can be laid on the surface of the agarose block after electrophoresis. The cellulose acetate membrane adsorbs surface proteins and, after appropriate staining (for example, with Coomassie Blue or other standard stain) serves to pinpoint the presence of protein in the agarose block. The appropriate sections of the block are then added to a beaker containing saline and analyses of the constituents are carried out as above.

Any other method for the specific detection of circulating antibody-antigen complexes can also be used. Two such techniques have been recently described in the patent literature. Masson et al, U.S. Pat. No. 4,062,935 describe a method of analyzing a sample for antibody-antigen complexes which includes a step of adding to the sample a solution of rheumatoid factor (RF) or $Cl_q$ (a component of complement) which have the property of combining with complexes but not with either free antigen or free antibody. Another, more efficient and general methodology is that given by Soothill et al, U.S. Pat. No. 4,141,965. Soothill et al describe a latex particle agglutination test useful for the determination of an immune complex which can readily be applicable to the present invention. A sample comprising the antibody-ACRT complex is incubated with coated latex particles and IgM antibodies, the latex particles being coated with milk reverse transcriptase and the IgM antibodies being low affinity antibodies raised against milk reverse transcriptase in a non-human animal. In the absence of antibody-ACRT complex, the latex particles will agglutinate. When however, antibody-ACRT complex is present in the serum, an inhibition of agglutination will be observed due to the interaction of the low affinity IgM with the ACRT-containing complex.

A latex particle agglutination technique can also be generally used for the detection of single constituents of the complex and therefore represents another available methodology for the detection of circulating ACRT or circulating antibody. This technique does not involve the use of a detectably labeled enzyme having reversible affinity for antibody but rather the use of the unlabeled enzyme itself. See for example, Sawai et al, U.S. Pat. No. 4,118,192 or Hoffmann-LaRoche, British Pat. No. 1,384,399. In these techniques, antibody raised against reverse transcriptase is supported on an insoluble carrier particle, usually a latex particle, thus sensitizing the insoluble carrier particle. The supported transcriptase immune IgG is then reacted with a sample suspected of containing the ACRT. The sensitized latex agglutinates to a degree which is proportional to the amount of ACRT present in the serum. The agglutination is followed by irradiating the resulting reaction mixture with light having a wave-length in the range of 0.6–2.4 microns. The determination of absorbance can be performed with a spectrophotometer similar to that used in near infrared spectrometry. Polystyrene latexes or styrene butadiene latexes can readily be used; however, other particles such as dispersed coccal bacteria, cell membrane fragments, micro particles of inorganic oxides such as silica, silica alumina, and alumina or finely pulverized minerals, metals and the like are also readily useable. These latex agglutination techniques not only make it possible to determine low concentrations of ACRT but enables the determination of the antigen in trace amounts and with comparable specificity to those of the ratioimmunoassay methodology. The amount of ACRT can be determined by measuring the absorbance as described above, or alternatively by measuring the rate of reaction, or the reaction time required for the absorbance to reach a perscribed value. When latex particles are coated with reverse transcriptase, agglutination thereof occurs when the serum sample contains antibody.

The Sawai et al methodology is also applicable in the inhibition of agglutination mode. In this mode, latex particles are coated with reverse transcriptase. The particles are then incubated with reverse transcriptase immune IgG. The so-formed complex is mixed with serum suspected of containing ACRT. If the serum sample contains ACRT, the latter will compete for the antibody binding sites and inhibit the agglutination of the enzyme-covered latex particles.

The techniques and materials of the present invention for the detection of breast cancer can be readily automated. A noteworthy development in the field of automated radioimmunoassay is the recent patent of Brooker et al, U.S. Pat. No. 4,022,577.

Among the kits useful in the present invention are those of the general type described by Szczesniak, U.S. Pat. No. 3,899,298. Such kits comprise a carrier being compartmented to receive at least one, or at least two, or at least three or more, containers and to maintain said containers in close confinement. A first container may contain detectably labeled reverse transcriptase. Another container may contain reverse transcriptase immune IgG raised in an appropriate animal. These materials may be in the freeze-dried state or suspended in a buffer solution. When in a freeze-dried state, the buffer solution may be in a third container. Alternatively, the complex of reverse transcriptase immune IgG and detectably labeled reverse transcriptase may be present in one container and buffer solution which may be added at the time of testing may be present in another container. Alternatively, the first container may be a test tube being coated at the inner surface thereof with reverse transcriptase immune IgG. A second container may contain detectably labeled reverse transcriptase in the presence or absence of buffer. At the time of testing for ACRT in the serum, the buffer suspension of labeled enzyme is added to the antibody coated test tube and a drop or two of the test serum containing the suspected antigen is added to the tube. Alternatively, the first container may be a test tube coated at its inner surfaces with reverse transcriptase immune IgG and containing in complexation therewith, the detectably labeled enzyme. At the time of testing, the addition of the suspect test sample is then sufficient to carry out the methodology. Other containers in the carrier may contain the elements necessary for the separation of bound and free detectably labeled enzyme. Thus, such containers may contain charcoal, silicates or second-antibodies useful in the "second antibody technique" described previously. Another container, for example, may contain detectably labeled anti-reverse transcriptase immune IgG for use in the determination of circulating anti-ACRT in the serum. Any number of variations and permutations consistent with the various techniques and for use in the detection of either ACRT, antibody or ACRT-antibody complex can be envisioned for the preparation of the kit. These are all matters of choice determined by the ease of handling, rapidity and efficiency of the testing.

The methodology of the present invention can be used to specifically diagnose the presence of breast cancer. ACRT, its antibodies or ACRT-antibody complexes are not present in non-lactating patients without breast cancer. Thre is no evidence that ACRT is present in patients with any other type of cancer. Since milk from lactating women contains the enzyme, it should be kept in mind that presence of the ACRT in serum may denote either breast cancer or lactation. This however isn't really a significant clinical problem. Less than 1% of women under 35 have breast cancer.

Having now generally described the invention, the same will be further illustrated by means of specific examples which are presented herewith for purposes of illustration only and are not intended to be limiting thereof, unless otherwise specified.

EXAMPLE 1

Isolation and Purification of Reverse Transcriptase from Human Milk

Figure 1:
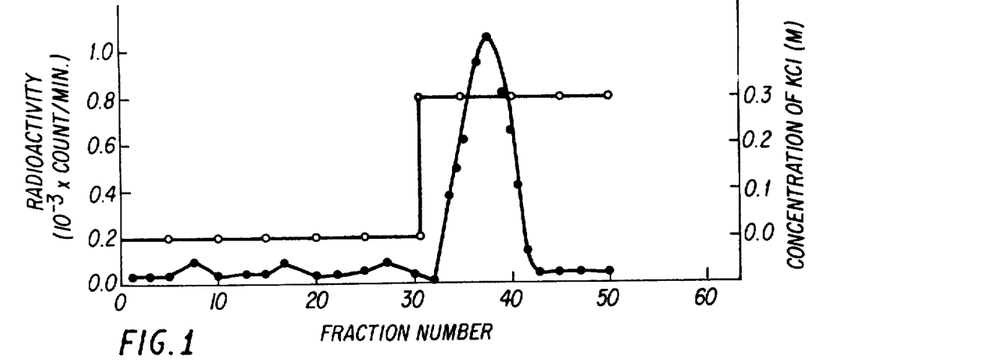
FIG. 1 shows the chromatographic elution profile of human milk DNA polymerase (reverse transcriptase) from a diethylaminoethyl-cellulose column (DEAE$^R$-cellulose).

Samples (N=10 to 20) of human milk were pooled (1 to 2 liters), defatted with 0.1 M EDTA (pH 8.3) and centrifuged at 2,500 g for 10 minutes at 40° C. The skim milk was filtered through two layers of cheesecloth, mixed with glycerol to a final concentration of 20%, and centrifuged at 48,000 rev/min for 90 minutes at 40° C. in a Beckman Ti-14 batch rotor. The fluid was aspirated and the outer wall of the rotor was scraped with a spatula and washed with 3 to 6 ml of 0.01 M tris-HCl (pH 8.0) (milk concentrate). Particles with a density ($\rho$) greater than 1.2 g/cm$^3$ were prepared according to a modification of the method described by Feldman et al (Proceedings of the National Academy of Sciences, USA, 70: 1976 (1973)). One ml of 1 M dithiothreitol was mixed with 1 ml of polyvinyl sulfate (1 mg/ml) and kept at 40° C.; 3 ml of the milk concentrate was then added to the tube followed by 100 µl of phospholipase C type 1 (10 mg/ml in 1% bovine serum albumin). The solution was incubated for 2 minutes at 37° C. and then for 20 minutes at 25° C. The solution was then placed in an ice bath, 3 ml of cold anhydrous ether was added, and after being mixed gently, the resulting emulsion was centrifuged at 1500 g for 10 minutes at 40° C. The lower aqueous phase was removed, and the ether was removed from the solution by blowing a gentle stream of filtered air over the surface for 5 to 10 minutes. The resulting solution was layered over a discontinuous metrazamide gradient consisting of 1.5 ml of 25% metrazamide and 1.0 ml of 18% metrazamide in TNE (10 mM tris-HCl (pH 8.0) at 150 mM NaCl, and 2 mM EDTA) and centrifuged for 90 minutes at 48,000 rev/min at 40° C. in a Spinco SW 50.1 rotor. The high density particles were resuspended in 0.01 M tris HCl (pH 8.0) containing 1% N-P$_{40}$ and 0.5 M KCl and were gently stirred for 1 hour at 40° C. The sample was desalted by centrifugation through 30 ml of coarse Sephadex G-25. The desalted material obtained by centrifugation through Sephadex G-25 was applied to a 10 ml column of DEAE-cellulose equilibrated with buffer A (10 mM tris HCl (pH 7.5), 20% glycerol, 0.2% N-P$_{40}$, and 2 mM DTT). After the sample was applied, the column was washed with 30 ml of buffer A and the DNA polymerase activity was batch-eluted with buffer A to which 0.3 M KCl had been added. Portions (10 µl) of each fraction from the DEAE-52 column and similar portions of fractions from subsequent column purification steps were assayed for polymerase activity with $(dG)_{12-18} \cdot (C)_n$ as described below. FIG. 1 shows the profile of the DEAE-cellulose column.

Figure 2:
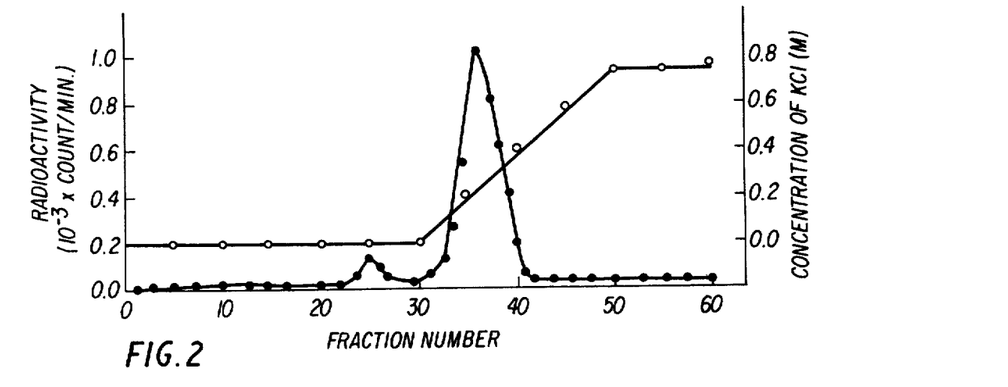
FIG. 2 shows the chromatographic elution profile of human milk DNA polymerase (reverse transcriptase) from a poly(C)agarose column.

The peak fractions from the DEAE-cellulose column were pooled, desalted by centrifugation through Sephadex G-25 and applied to a 3-ml poly(C)agarose column equilibrated in buffer A. The column was washed with 10 ml buffer A and the DNA polymerase activity was eluted with a 15 ml linear gradient of 0 to 0.8 M KCl in buffer A. The peak enzyme activity was eluted at 0.22 M KCl. The fractions containing the main peak of DNA polymerase activity were pooled and ovalbumin was added to 200 µg/ml. This material was kept at 4° C. and was used as the starting material for characterization studies. FIG. 2 shows the poly(C)agarose column profile.

Enzymatic Assay for the Reverse Transcriptase Enzyme

Enzymatic activity of the human milk DNA polymerase with various synthetic polynucleotides was determined as follows: assay mixtures containing 10 µl of enzyme were initiated by adding 40 µl of a mixture that gave a final concentration of 50 mM tris-HCl (pH 8.0); 60 mM KCl; 1 mM DTT; either 10 mM MgCl$_2$ or 0.5 mM MnCl$_2$, 7.6 µM [$^3$H] TTP (2,000 to 4,000 counts per minute per picomole, or 7.6 µM [$^3$H] dGTP (2,000 to 4,000 counts per minute per picomole); and bovine serum albumin (0.5 mg/ml). All reactions were performed at 37° C. for 30 minutes. Acid insoluble precipitates were collected on filters and the radioactivity was counted by means of a liquid scintillation counting system.

EXAMPLE 2

Characterization of Reverse Transcriptase from Human Milk (Molecular Weight)

Figure 3:
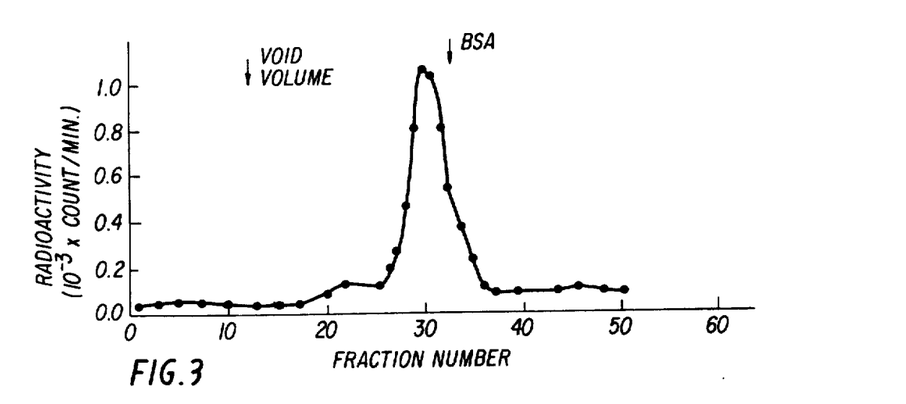
FIG. 3 shows the chromatographic elution profile of human milk DNA polymerase (reverse transcriptase) from a Sephadex® (bead-formed dextran gel cross-linked with epichlorohydrin).

The enzyme-active fractions from the poly(C)agarose column from Example 1 were pooled and applied to a 20-ml Sephadex G-200 column equilibrated in buffer A containing 0.5 M KCl. The column had been standardized with ovalbuminum (43,000), bovine serum albumin (68,000), and phosphorilase A (93,000). Fractions (250 µl) were collected and 10-µl portions were assayed for DNA polymerase activity with $(dT)_{12-18} \cdot (A)_n$. The milk DNA polymerase eluted 2 to 3 fractions before bovine serum albumin indicating an apparent molecular weight of 70,000. The Sephadex G-200 chromatography profile is shown in FIG. 3.

EXAMPLE 3

Figure 4:
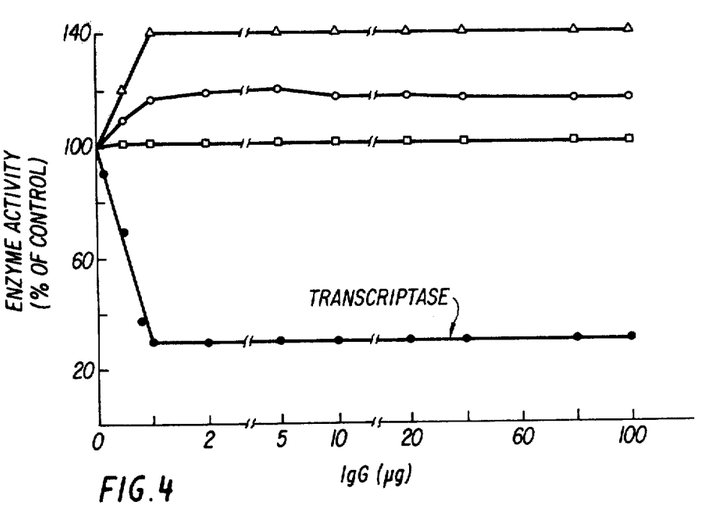
FIG. 4 shows the comparative inhibition of the human milk reverse transcriptase and polymerase $\alpha,\beta$ and $\gamma$ by IgG directed against the human milk reverse transcriptase. Enzyme activity in the presence of immune IgG is expressed as a percentage of the activity in the presence of an identical amount of control IgG. Symbols:      : polymerase $\alpha$; □: polymerase $\beta$; △: polymerase $\gamma$, and      : reverse transcriptase.
Figure 5:
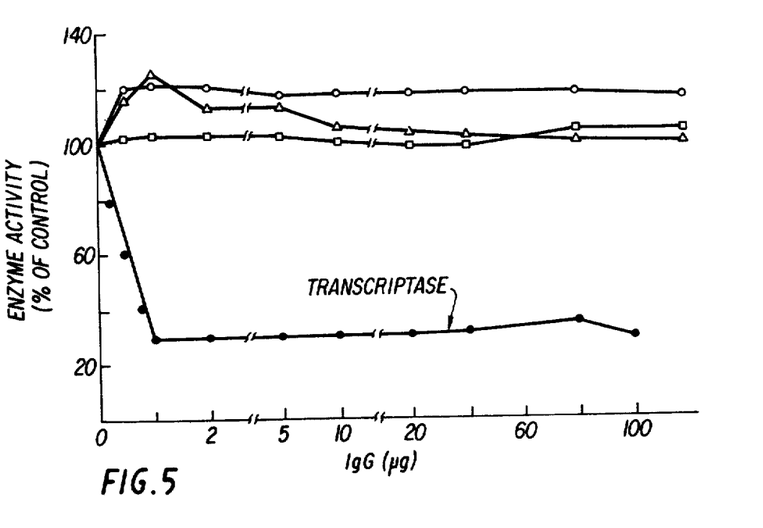
FIG. 5 shows the titration of DNA polymerases from other human sources against IgG to human milk reverse transcriptase. Symbols:      : polymerase $\alpha$ from NC-37 cells; △: polymerase $\gamma$ from NC-37 cells; □: polymerase $\gamma$ from HeLa cells; and      : reverse transcriptase from human milk.

Comparative Inhibition of Human Milk Reverse Transcriptase and Human Polymerase $\alpha, \beta$ and $\gamma$ by IgG Directed Against the Human Milk Reverse Transcriptase FIGS. 4 and 5 show antibody neutralization studies of partially purified human milk DNA polymerases with IgG fraction of antibody to human reverse transcriptase. Enzyme activity in the presence of immune IgG is expressed as a percentage of the activity in the presence of an identical amount of control IgG. The results demonstrate that immune IgG against reverse transcriptase (anti-reverse transcriptase) inhibited the reverse transcriptase 70% but did not inhibit polymerases $\alpha, \beta$ or $\gamma$ from human milk (FIG. 4). Neither DNA polymerase $\alpha$ from human lymphoid cells nor DNA polymerase $\gamma$ from NC-37 cells or from HeLa cells was inhibited by the antibody to reverse transcriptase (FIG. 5).

EXAMPLE 4

Preparation of Reverse Transcriptase Immune IgG

A solution containing 200 µg of human milk DNA polymerase (reverse transcriptase) obtained from the poly(C)agarose column was divided into 8 portions of 1 ml each. For the first two immunizations, a portion of the transcriptase (25 µg) was emulsified with an equal volume of complete Freund's adjuvant and injected into 6 subcutaneous sites on the back of a New Zealand rabbit. Subsequent immunizations were made at weekly intervals and were similarly performed except that incomplete adjuvant was used. A total of 8 immunizations were performed and the animal was bled from the ear vein at the end of the 8th week. Samples (50 ml) of blood were taken, the serum was recovered, and the IgG fraction was purified by precipitation with 50% ammonium sulfate and by DEAE-52 cellulose chromatography. The purified IgG fractions were free of ribonuclease and deoxyribonuclease activity. Normal (nonimmune) IgG was similarly purified from serum obtained from the same rabbit prior to immunization. The IgG fractions were dyalized against 0.01 M tris-HCl (pH 8.0) and stored at −70° C. The protein concentration of IgG was determined by optical absorption at 280 nm, with an assured extinction coefficient for a 1% solution and a 1 cm path length of 14.2 (Little, J. R. et al, Methods in Immunology and Immunochemistry, 2: 343 (1969)).

Having now generally described this invention, it will be apparent to one of ordinary skill in the art that the same can be carried out with minor modifications or changes which do not affect the content or spirit thereof.

We claim:

1. A method for diagnosing mammalian breast cancer by detecting, in a physiological fluid of said mammal, antibodies having immuno-reactivity towards human reverse transcriptase, which comprises:

mixing a sample of said fluid containing said antibodies with an excess of reverse transcriptase substantially purified having a molecular weight of about 70,000 and a sedimentation coefficient on a glycerol gradient of between 5 and 5.5 S, and being capable of binding to said antibody and of forming a complex therewith, and;

detecting said complex.

2. The method of claim 1, which further comprises separating said complex from said excess reverse transcriptase.

3. The method of claim 1, wherein said substantially purified reverse transcriptase is detectably labeled.

4. The method of claim 3, wherein said label is selected from the group consisting of a chromophore, a radiolabel, and an enzyme label.

5. The method of claim 4, wherein said radiolabel is $^{125}I$.

6. The method of claim 5, wherein said detection is carried out by scintillation counting.

7. The method of claim 1, wherein said detection is carried out by a colorimetric assay.

8. The method of claim 1, wherein said detection is carried out by adding to said mixture a second antibody raised against said first antibodies in said fluid.

9. The method of claim 8, wherein said second antibody is detectably labeled.

10. The method of claim 9, wherein said label is an enzyme.

11. The method of claims 9 or 10, wherein the reverse transcriptase is bound on a water insoluble support.

12. The method of claim 11, wherein said support is a strip of plastic or cellulose.

13. A method of diagnosing mammalian breast cancer by detecting, in a physiological fluid of said mammal, a complex of an antigen (ACRT) having cross-reactivity towards human reverse transcriptase and an antibody therefor, wherein said reverse transcriptase is substantially purified, has a molecular weight of about 70,000 and a sedimentation coefficient on a glycerol gradient of between 5 and 5.5 S.

14. The method of claim 13, which further comprises separating said complex into its individual components and then detecting the individual components.

15. The method of claim 14, wherein said separation is carried out by acidifying a solution containing said complex in the presence of polyethyleneglycol of molecular weight 6000.

16. The method of claim 15, which further comprises electrophoresing said mixture of components of ACRT, antibody and polyethylene-glycol on an agarose-containing material.

17. The method of claim 14, wherein said component being detected is an antibody.

18. The method of claim 14, wherein said component being detected is ACRT.

19. In a method of diagnosing mammalian breast cancer by immunoassay, the improvement which comprises detecting in a physiological fluid of said mammal a material selected from the group consisting of a complex of an antigen (ACRT) having immune cross-reactivity with human reverse transcriptase enzyme with an antibody therefor, and an antibody against ACRT.

20. The method of claim 19 wherein said reverse transcriptase enzyme is from human milk.

21. The method of claim 8 wherein said second antibody is obtained from a hybridoma from human or nonhuman animal sources.

22. The method of claim 19 wherein said material being detected is an antibody against ACRT.

23. The method of claim 19 wherein said material being detected is a complex of ACRT with an antibody therefor.

24. The method of any of claims 1, 13 or 19 wherein said human reverse transcriptase enzyme is substantially purified from human milk.

* * * * *